United States Patent [19]

Tureaud

[11] 4,184,253
[45] Jan. 22, 1980

[54] DENTURE AND METHOD OF PRODUCING AND FITTING

[75] Inventor: Kenneth E. Tureaud, Ann Arbor, Mich.

[73] Assignee: Warner-Lambert Company, Morris Plains, N.J.

[21] Appl. No.: 859,611

[22] Filed: Dec. 12, 1977

[51] Int. Cl.² ............................................. A61C 13/00
[52] U.S. Cl. ................................................... 433/171
[58] Field of Search .................... 32/2, 71; 264/17, 18

[56] References Cited

U.S. PATENT DOCUMENTS

| 391,062 | 10/1888 | Miller | 32/2 |
|---|---|---|---|
| 2,308,457 | 1/1943 | Saffir | 32/71 |
| 2,341,154 | 2/1944 | Myerson | 32/71 |
| 2,341,156 | 2/1944 | Myerson | 32/71 |
| 3,316,639 | 5/1967 | Shovers | 32/2 |
| 3,846,911 | 11/1974 | Wichner | 32/2 |
| 4,012,838 | 3/1977 | Abdenour | 32/2 |
| 4,017,971 | 4/1977 | Hazar | 32/2 |

*Primary Examiner*—Louis G. Mancene
*Assistant Examiner*—John J. Wilson

*Attorney, Agent, or Firm*—David B. Ehrlinger; Frank S. Chow; Stephen Raines

[57] ABSTRACT

A prosthetic preform comprised of a hard base into which are molded the posterior prosthetic teeth, with the anterior prosthetic teeth being mounted in a waxy material contained in a cavity or cavities disposed in the hard base. The preform is further provided with a formable deflectable layer secured to the hard base structure and adapted to be fit to the general contours of the wearer's mouth with an impression material used to line the tissue surface of the deflectable layer to obtain an impression of the intimate detail of the edentulous tissue. The anterior teeth may thus be adjusted in position during fitting and/or anatomical features carved. A mold is made of the anterior teeth and exposed waxy material after fitting which allows casting the fitted anterior teeth in hard base material to the remainder of the hard base structure. The preform may be directly used to provide a prosthetic denture by using an impression material which is bondable to and cures the deflectable layer, or alternatively the fitted preform may be conventionally flasked and hard base material cast around and to the hard base in a resultant mold cavity after removal of the deflectable layer.

12 Claims, 9 Drawing Figures

DENTURE AND METHOD OF PRODUCING AND FITTING

BACKGROUND OF THE INVENTION

1. Field of the Invention.

This invention concerns prosthetic dentures of the type wherein either the maxillary or mandibular natural dentition is to be replaced by the prostheses.

2. Description of the Prior Art.

A major concern in the design and manufacture of such prosthetic dentures is the fit of the dentures to the edentulous area of the patient's mouth and also the position of the teeth with respect to the wearer's mouth to produce a natural appearance. The fit to the oral tissues, particularly the edentulous gum area of the patient's mouth is critical in the comfort, wearability and aesthetic appearance of the denture and the difficulty in obtaining suitable fit accounts in large part for the cost of providing high quality dentures.

The material which has been developed for prosthetic teeth and gums, i.e., acrylic plastic, has very suitable characteristics in many respects, but the material cannot be directly formed and cured within the patient's mouth due to the difficulty in curing the mass of plastic material which constitutes the complete denture. The use of other materials has been attempted but the bonding of such materials to the prosthetic teeth has not been adequately rigid to prevent the deflection of the teeth and the base material during chewing. This allows gaps to open up during chewing and the denture thus entraps food particles and the denture is thus difficult to keep clean.

It has been proposed and utilized in the past prosthetic dentures in which a hard unitary base structure is provided, with the prosthetic teeth being arranged in a rigid unitary structure extending in a generally U-shape, to which is bonded a soft deflectable liner layer which is formable at relatively low to moderate temperatures compatible with the comfort of the patient during fitting. This liner layer has upward extending flange areas which can be shaped into general conformance with the contacted oral tissues. An intimate fitting is then carried out by lining the deflectable liner layer with a soft, impressionable and hardenable layer coated on the tissue surfaces or disposed on the liner layer after the initial fitting.

A subsequent fitting allows the accurate fitting of the denture to the intimate detail of the patient's mouth, and the denture is then allowed to partially set within the patient's mouth with the curing completed after removal.

This last-mentioned layer also fixes the deflectable liner layer which has previously been partially hardened by freeze spraying or a cold water or ice bath.

This method produces a denture which has adequate rigidity characteristics.

Copending application, Ser. No. 835,143, filed Sept. 21, 1977, solves one problem in this method by taking another approach in the design of the denture: Instead of providing a unitary rigid hard base structure, there is provided a segmented hard base structure, in which individual hard base structure segments are adjustable with respect to each other, allowing a much more accurate alignment of the prosthetic teeth with the mandibular or maxillary gum ridge lines. Alignment of the denture with the gum ridges was a problem with the aforementioned method since the position of the teeth could not be changed during fitting.

Another problem inherent with this approach is that it would be desirable if the incisor teeth and/or cavities were able to be repositioned for purposes of obtaining a more natural appearance and proper bite, or to accommodate existing natural dentition. The use of hard unitary rigid base structure to which the prosthetic teeth are molded precludes any such adjustment at the time of fitting of the denture.

Accordingly, it is an object of the present invention to provide a prosthetic preform in which the position of the anterior teeth may be adjusted during the fitting and in which the anterior teeth thereafter may be molded within a hard rigid base material similar to the base material used to anchor the posterior teeth, to produce a very secure anchoring of these teeth in the prosthetic denture while accommodating such adjustments.

It is a further object of the present invention to provide a method of manufacturing a denture from the fitting impressions taken during the fitting of prosthetic preforms to the wearer's edentulous tissues, either directly by the fitted and cured preform, or from a casting made from flasking the fitted preform in a conventional manner.

SUMMARY OF THE INVENTION

These and other objects of the present invention, which will become apparent upon a reading of the following specification and claims, are accomplished by a prosthetic preform device in which the prosthetic anterior teeth are anchored within the hard base structure segments and to which is bonded a soft deflectable liner layer adapted to be fitted to the edentulous tissue contours and subsequently intimately fitted thereto by the use of a hardenable impression material disposed on the surface contacting the tissue of the deflectable liner layer after the initial fitting with a subsequent refitting obtaining the intimate fit. The anterior teeth are retained within the denture in a waxy material deposited within a cavity formed in the deflectable liner layer so that during the fitting procedures the position of the anterior teeth may be adjusted or they may be removed. A matrix or mold impression is made of the anterior teeth after the denture fitting and the wax then removed from the cavity and a hard base material cast into the resulting cavity to mold the anterior prosthetic teeth into the material and to bond it to the hard base structure segments carrying the posterior teeth to produce a hard base structure for both anterior and posterior teeth.

The preform may be directly used to provide a prosthetic denture by using an impression material which is bondable to and cures the deflectable layer, or alternatively the fitted preform may be conventionally flasked and hard base material cast around and to the hard base in a resultant mold cavity after removal of the deflectable layer. The hard base material may be comprised of a hard acrylic plastic while the deflectable liner layer may be provided by a soft deflectable acrylic plastic.

DETAILED DESCRIPTION

In the following detailed description, certain specific terminology will be utilized for the sake of clarity and a specific embodiment described in accordance with the requirements of 35 USC 112, but it is to be understood that the same is not intended to be limiting and should not be so construed inasmuch as the invention concepts set forth in the appended claims are susceptible of taking many forms and variations within the scope of the appended claims.

Figure 1:
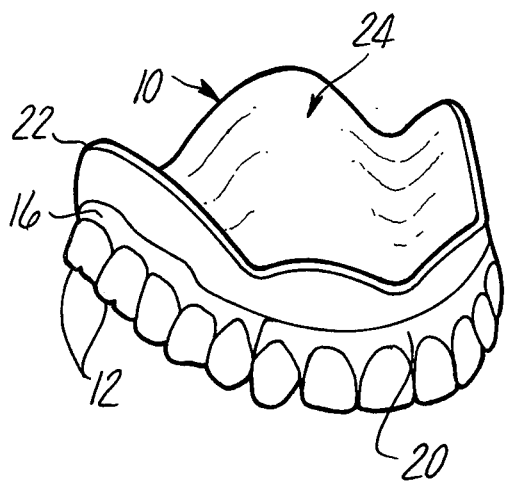
FIG. 1 is a perspective view of a prosthetic denture preform according to the present invention.
Figure 2:
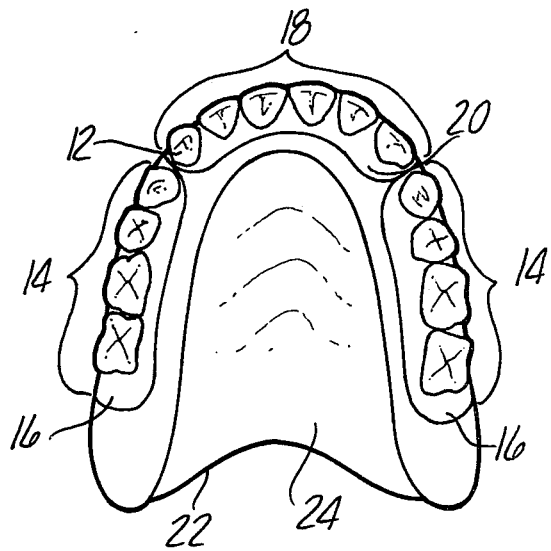
FIG. 2 is a plan view of the prosthetic denture preform according to the present invention shown in FIG. 1.

Referring to the drawings and particularly FIGS. 1 and 2, the prosthetic denture preform 10 is illustrated in these FIGURES as a maxillary denture including a set of prosthetic teeth 12 formed from appropriate materials such as hardened acrylic plastic, the prosthetic teeth 12 shaped and located to correspond to human dentition. According to the concept of the present invention, the prosthetic teeth 12 are grouped into three groups, two alternate posterior tooth sets, each molded within a hard base structure segment 14 of a material such as a hardened acrylic plastic, while the anterior teeth set has the anterior prosthetic teeth 18 embedded within a waxy, formable material such as a mass of investment casting wax 20 contained within a cavity or cavities 28.

Both the hardened base material segments 16 have bonded thereto a soft deflectable formable liner layer 22 which may be formed from unhardened acrylic plastic. The soft deflectable formable liner layer 22 has posterior margins and an anterior margin. The hardened base material 16 is bonded to the liner layer 22 at its posterior margins. The mass of waxy material 20 is disposed within a cavity or cavities in the frontal portion at the anterior margin of the liner layer 22. The soft deflectably formable liner layer 22 is formed with upwardly extending peripheral flanges in approximate configuration corresponding to the edentulous gum area and the oral tissues of the human mouth for the maxillary version of the denture shown with a palatal vault liner 24 provided.

The result of the disposition of the anterior teeth 18 in the mass of wax material 20 is to allow an adjustment in position of the individual teeth and carving of anatomical features during the normal fitting of the prosthetic denture preform 10 of this type.

In practice, the denture preform 10 is placed within the patient's mouth after slight heating of the deflectably formable liner layer 22 to render it pliable, the liner layer 22 shaped into general conformity with the contours of the wearer's mouth into contact with the liner layer 22 in the appropriate alignment of the denture preform 10 within the patient's mouth, the anterior prosthetic teeth 18 are then adjusted as desired in position with the waxy material accommodating this adjustment. The denture is then removed and a soft or liquid layer of hardenable material (such as a coating of liquid acrylic) is placed or coated on the top of the deflectable layer 22. The denture preform 10 is repositioned in the wearer's mouth to provide intimate conformance of the upper surface of the denture to the edentulous tissue.

Prior to this step, the soft deflectable liner layer 22 may be fixed by a freeze spray or other such means of chilling the material to provide an adequately firm support for this subsequent final fitting step. The layer of coating of hardenable impression material is then allowed to set in the patient's mouth to preserve the impression formed by the patient's edentulous mouth.

Figure 3:
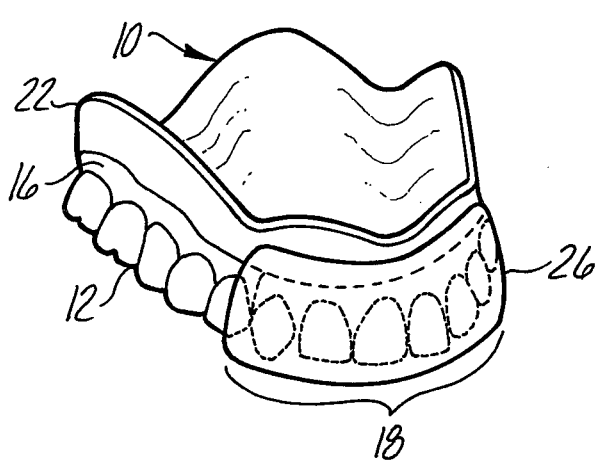
FIG. 3 is a perspective view of a prosthetic denture preform according to the present invention which has been fit to the wearer's mouth and to which molding material has been applied to the anterior teeth and adjacent exposed waxy material.
Figure 4:
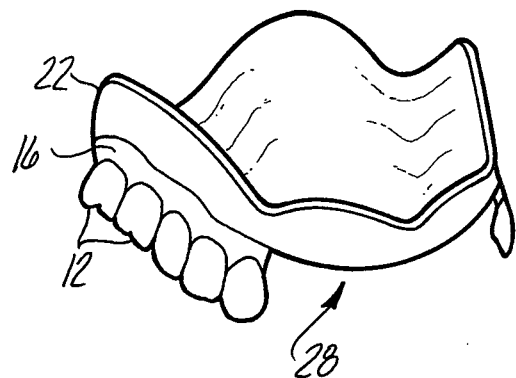
FIG. 4 is a perspective view of the prosthetic denture preform shown in FIG. 3 with the anterior teeth removed to remove the waxy material into which the anterior teeth were temporarily set.

The final fixation of the anterior teeth 18 is accomplished by first forming a matrix or mold 26 by packing of appropriate dental material about the anterior prosthetic teeth 18 as shown in FIG. 3. After setting of the mold 26, it is then removed with the anterior prosthetic teeth 18 set within the mold and the waxy material melted out which leaves cavity 28 (FIG. 4).

Figure 5:
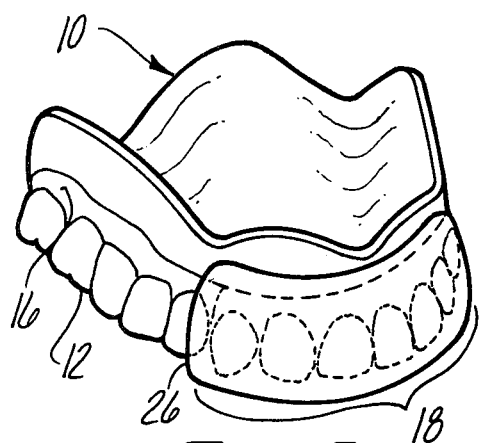
FIG. 5 shows a perspective view with the mold of the denture shown in FIG. 4 in position.
Figure 6:
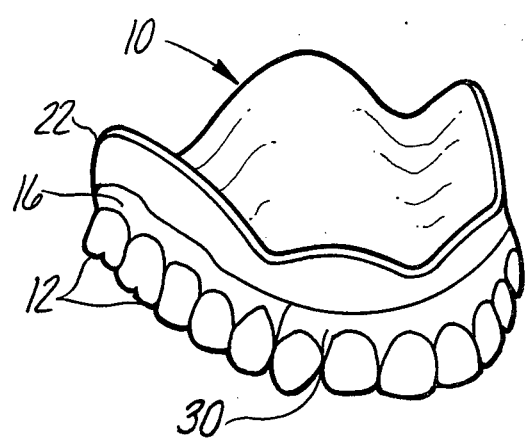
FIG. 6 is a perspective view of the completed prosthetic denture according to the present invention.

In FIG. 5, the mold 26, still carrying the anterior prosthetic teeth 18 so as to maintain them in precise adjusted relative position, is repositioned with respect to the denture preform 10 as shown in FIG. 5 by location on the adjacent posterior segments 14 and the surface of the deflectably formable liner layer 22. The void created by the removal of the casting wax 20 is then filled with a hard acrylic material similar to that forming the hard base segments into which is embedded the posterior prosthetic teeth 12 which material hardens and bonds to the posterior segments 14 so as to form a hard rigid unitary support for the anterior prosthetic teeth 18 by the resulting cast-in hard base segment 30 occupying the void formerly occupied by the mass of wax 20.

The fitted denture preform 10 is then smoothed by deburring, polishing, etc., to provide a finished denture.

It can be appreciated that the prosthetic teeth are very firmly bonded in the completed denture by being molded or fused within the material to provide a very well fitting, comfortable denture which may provide rigid support for the prosthetic teeth.

If a denture of all-hardened acrylic material is desired rather than one having a bonded liner layer as described, the prosthetic denture produced by the aforementioned process can be used with the deflectable soft liner layer 22 providing an impression taking surface for use in a subsequent conventional casting procedure.

In this procedure, the deflectable liner layer 22 is used as a temporary mold-impression making model. In this application, the soft deflectable liner layer 22 is not permanently bonded to the hard base segments 14 and 30, but is strippably joined thereto. An elastomeric material is used for the impression layer 40 (FIG. 7) during the intimate fitting of the denture to the patient's edentulous tissue after the deflectable liner layer 22 has been shaped to the general contours of the patient's mouth, as in the above procedure.

Figure 7:
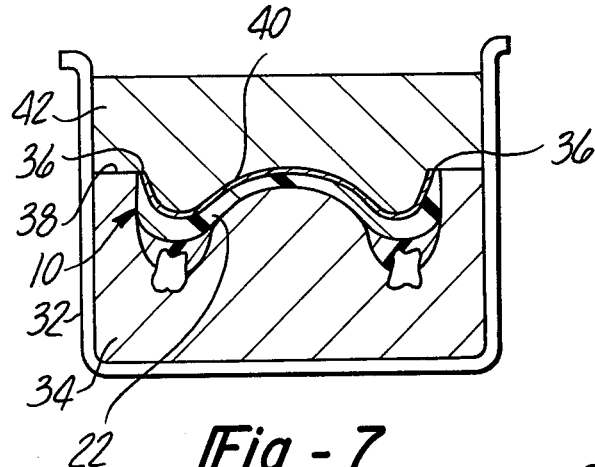
FIG. 7 is a sectional view of a fitted prosthetic denture preform according to the present invention shown in position within a flask during formation of the molds used in the manufacture of a prosthetic denture from the fitted preform.
Figure 8:
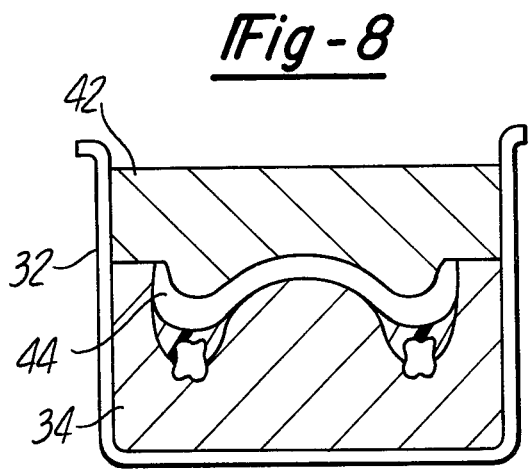
FIG. 8 is a sectional view of the denture preform and flask shown in FIG. 7, with the deflectable liner layer stripped from the hard base structure in which are mounted the prosthetic teeth.

The denture preform 10 so shaped is then flasked in a conventional manner, in which it is embedded in molding material 34 up to the level of the upper periphery 36 of the denture preform 10, as shown in FIG. 7. The upper portion 42 of the resultant mold is removed and the deflectably formable liner layer 22 and the impression layer 40 are then both stripped away leaving a mold cavity 44 as shown in FIG. 8.

Figure 9:
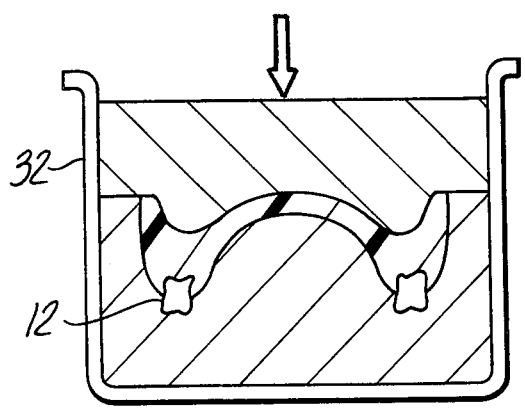
FIG. 9 is a sectional view of the mold shown in FIG. 8 and a prosthetic denture formed by casting a hard base material into the cavity formed by stripping the deflectable liner layer from the mold.

The mold cavity 44 is then injected with a hard cold or heat curable acrylic plastic to form a unitary or an all-hard acrylic supported prosthetic teeth 12 and 18, as shown in FIG. 9, with the entire mold cavity filled with the hardened acrylic plastic so that the resultant structure is a unitary rigid denture.

The denture so produced is removed from the flask 32 after hardening, and final polishing and other finishing steps are carried out.

It can be seen that the resultant denture would be perfectly fitting, while being rigid in construction.

Many variations in specifics are of course possible, such as in the materials used and the precise details of the steps described.

The embodiments of the invention in which an exclusive property or privilege is claimed are defined as follows:

1. A denture preform device comprising:
   a plurality of prosthetic teeth corresponding in shape and position to human maxillary and mandibular dentition, said prosthetic teeth being arranged into two groups, each comprised of a set of posterior prosthetic teeth molded into a hard base structure segment of hard base material;
   a soft deflectably formable liner layer having posterior margins and an anterior margin therebetween, said margins defining an arch generally parallel to posterior and anterior teeth, the posterior margins being bonded to said hard base structure segments and said liner layer having peripheral flange areas in general conformance with human edentulous tissue;
   at least one cavity formed in said deflectably formable liner layer, the cavity being located at said anterior margin intermediate said hard base structure segments and being filled with a mass of deflectably formable material;
   a plurality of anterior prosthetic teeth corresponding in shape to human dentition, embedded into said deflectably formable material in positions corresponding to human dentition, whereby the position of said anterior prosthetic teeth is adjustable in final fitting and said teeth after removal can be precisely repositioned with respect to the denture preform by location on the adjacent posterior segments and the anterior margin of said liner layer;
   said material filling said cavity being removable from said cavity for casting in of a permanent hard base structure about said anterior teeth.

2. The denture preform device according to claim 1 wherein said formable material filling said cavity comprises a waxy material.

3. The denture preform device according to claim 1 wherein said hard base structure segments are formed of a hardened acrylic plastic.

4. The denture preform device according to claim 3 wherein said soft deflectably formable liner layer is formed of a soft deflectable acrylic plastic bonded to said hard base structure segments.

5. A method of producing and fitting a prosthetic denture comprising:
   providing a denture preform device consisting of a set of prosthetic teeth shaped and mounted in position in correspondence with natural human dentition, said prosthetic teeth mounted in groups, including two sets of posterior prosthetic teeth molded into hard base structure segments and the remaining anterior prosthetic teeth mounted in a mass of formable material contained in at least one cavity disposed between said hard base segments, and further including a soft deflectably formable liner layer having posterior margins and an anterior margin therebetween, said margins defining an arch generally parallel to posterior and anterior teeth, the posterior margins being bonded to said hard base segments and having peripheral flange areas in general conformance with human edentulous tissue;
   placing said prosthetic preform device in the mouth of a person to be fitted and shaping the deflectably formable liner layer into a general conformance with the edentulous tissue and positioning the anterior teeth for optimum fit and aesthetic appearance;
   removing the denture preform and disposing a soft impressionable layer of material on the tissue surface of the deflectably formable liner layer after fixing the deflectably formable liner layer, and repositioning the denture preform within the person's mouth for forming the tissue surface into intimate conformity with the edentulous tissue;
   removing said prosthetic denture preform after setting of said impression material;
   molding material about said group of anterior prosthetic teeth to surround said anterior prosthetic teeth and said mass of formable material;
   removing said anterior prosthetic teeth with said mold and removing said mass of formable material from said anterior prosthetic teeth;
   repositioning said anterior teeth carried by said mold in said prosthetic denture;
   casting a hard base material in the void left by removal of said mass of formable material to produce a hard base structure for said anterior prosthetic teeth.

6. The method of producing said prosthetic denture according to claim 5 wherein in said step of filling said cavity with a formable material, said cavity is filled with a waxy material.

7. The method of producing said prosthetic denture according to claim 5 wherein said hard base structure segments are formed of a hardened acrylic plastic.

8. The method of producing said prosthetic denture according to claim 7 wherein said soft deflectably formable liner layer is formed of a soft deflectable material bonded to said hard base structure segments.

9. A method of producing and fitting a prosthetic denture formed entirely of a hard base structure material according to claim 5;
   stripping said deflectably formable liner layer and impressionable material while said denture preform is positioned with the lower surface embedded within one of said mold portions;
   replacing the other mold portion;
   casting hard base structure material into the void created by stripping said deflectably formable liner layer and impressionable material, whereby a prosthetic denture is provided in which said prosthetic teeth are mounted entirely in hard base structure material.

10. The method according to claim 9 wherein said hard base structure material is hardened acrylic plastic.

11. The prosthetic denture produced by the method of claim 5.

12. The prosthetic denture produced by the method of claim 9.

* * * * *